United States Patent [19]

Kross

[11] Patent Number: 5,622,725
[45] Date of Patent: Apr. 22, 1997

[54] WOUND DISINFECTION AND REPAIR

[75] Inventor: Robert D. Kross, Bellmore, N.Y.

[73] Assignee: Alcide Corporation, Redmond, Wash.

[21] Appl. No.: 672,686

[22] Filed: Jun. 28, 1996

Related U.S. Application Data

[63] Continuation of Ser. No. 206,062, Mar. 4, 1994, abandoned, which is a continuation-in-part of Ser. No. 133,465, Oct. 8, 1993, which is a continuation-in-part of Ser. No. 854,286, Mar. 20, 1992, Pat. No. 5,252,343.

[51] Int. Cl.$^6$ .......................... A61K 33/20; A61K 33/40; A01N 59/00
[52] U.S. Cl. .......................... 424/665; 424/661; 424/662; 424/663; 424/664; 422/28; 422/29; 422/37; 604/29; 604/53; 210/636
[58] Field of Search ..................... 424/661–665; 422/28, 29, 37; 604/29, 53; 210/636

[56] References Cited

U.S. PATENT DOCUMENTS

| | | | |
|---|---|---|---|
| 4,956,184 | 9/1990 | Kross | 424/661 |
| 4,986,990 | 1/1991 | Davidson | 424/665 |
| 5,019,402 | 5/1991 | Kross | 424/665 |
| 5,252,343 | 10/1993 | Kross | 424/661 |
| 5,389,384 | 2/1995 | Jooste | 424/661 |

OTHER PUBLICATIONS

Dennis, Jr. et al., "Sepsis of Vascular catheters . . . " Journal of Biomedical Materials Research, vol. 24(1), 1990, pp. 95–105.

Ninikowski, Jr. et al., in Janssen et al. (eds.), Wound Healing, Wrightson Biomedical Publishing Ltd., Peterfield (UK), 1991, pp. 165, 169, 173 and 174.

Cohen, I.K., et al., eds, Wound Healing, W.B. Saunders Co., Philadelphia (1992) pp. 24, 146–147, 292, 298, 302–303, 576, 584–586.

Hau, T., and Nishikawa, R., Surg. Gyn. & Obstet. 156: 25–30 (1983).

Kenyon, A.J., et al., Am. J. Vet Res. 47: 96–101 (1986).

Wyngaarden, J.B., et al, Cecil's Textbook of Medicine, 19th ed., Harcourt Brace Javanovich, Philadelphia, 1992, pp. 541–545.

*Primary Examiner*—John Pak
*Attorney, Agent, or Firm*—Seed and Berry LLP

[57] ABSTRACT

Methods for preventing and treating microbial wound infections, especially of peritoneal cavity wounds including those having indwelling catheters, and enhancing wound repair while minimizing adhesions and scar formation involve the infusion or irrigation of the wound with a solution containing a pharmacologically acceptable carrier and chlorine dioxide in an amount ranging from about 5 ppm to 1000 ppm, and having a chlorine dioxide to chlorite ratio of at least 5:1. Typical solutions contain chlorine dioxide in isotonic saline and exhibit a pH of from about 5 to about 7.5. Sodium chlorite is employed in preferred embodiments.

25 Claims, 3 Drawing Sheets

WOUND DISINFECTION AND REPAIR

CROSS-REFERENCE TO RELATED APPLICATIONS

This application is a continuation of U.S. patent application Ser. No. 08/206,062, filed Mar. 4, 1994, now abandoned, which is a continuation-in-part of copending U.S. application Ser. No. 08/133,465, filed Oct. 8, 1993, which is a continuation-in-part of U.S. application Ser. No. 07/854,286, filed Mar. 20, 1992, which issued as U.S. Pat. No. 5,252,343 on Oct. 12, 1993.

TECHNICAL FIELD

This invention relates generally to the disinfection and repair of wounds, especially peritoneal cavity wounds and surgical sites.

BACKGROUND OF THE INVENTION

With the possible exception of teeth, tissues and organs of the body are capable of repairing injuries. An injury may be broadly defined as an interruption in the continuity of tissues, and these are repaired by reestablishing that continuity. Tissue repair is achieved primarily by proliferation, migration and differentiation of involved cells. Epithelial tissue heals chiefly by cellular migration, presumably because epithelium is essentially two-dimensional. With mesodermal tissues, however, the three-dimensional configuration is correlated with a somewhat different mode of repair that takes the form of an aggregate of cells that migrate into the lesion where they eventually redifferentiate into the tissue in question. These repair aggregates may take the form of granulation tissue in the case of dermis, fracture callus in the case of broken bones, or a comparable accumulation of cells between the cut ends of a severed tendon. (For a very brief review, see Cohen, I. K., et al., eds., Wound Healing, W. B. Saunders Co., Philadelphia, 1992, page 24).

The physiological process of wound healing or tissue repair has been arbitrarily divided into three major phases: the inflammatory phase, the proliferative phase, and the remodeling phase. A complex series of physiological and biochemical events can be correlated with macroscopic and microscopic changes in the wound as it heals.

The first, or inflammatory, phase of wound repair is initiated by a sequence of biochemical and cellular events that begins once the integrity and homeostasis of the tissue membranes are disrupted and involves both humoral and cellular components. A commonly observed feature of inflammation is the release of various eicosanoids and the appearance of polymophonuclear neutrophils, which migrate into both infected and noninfected wounds. The neutrophils are followed by monocytic macrophages that remove wound debris and contribute soluble mediators including additional eicosanoids that promote wound repair.

In infected wounds or in wounds with massive tissue destruction, the process of phagocytosis by both cell types is accompanied by a sequence of biochemical events that sharply increase oxygen uptake, producing a number of oxygen-derived free radicals including superoxide, hydroxyl and singlet oxygen, and derivative products such as hydrogen peroxide. These reactive products generate chemotactic factors for phagocytes and may be used by the phagocyte in destruction of infectious wound contaminants, but phagocyte-derived oxygen reduction products can also cause tissue damage and mediate ischemic injury (id., pages 302 to 303). Increased levels of inflammatory mediators, especially the vasoconstrictive ones, have been shown experimentally to enhance bacterial proliferation and microabscess formation. In infected wounds, this sets up a vicious cycle resulting in an imbalance of mediators normally useful in the repair process (id., pages 292 and 298).

In man, collagen plays a pivotal structural role in the proliferative and remodelling phases of wound healing and tissue repair (id., pages 146 to 147). The collagenous scaffold of the extracellular matrix comprises at least 13 genetically distinct types of collagen (ibid.), and the role the types play in the pathophysiology of tissue repair and their interplay with noncollagenous matrix materials is incompletely understood, especially the more recently described collagen types VI to XIII. In general, however, it has been observed that connective tissue reaction to injury eventually leads to the appearance of increased numbers of fibroblasts and finally to the accumulation of numerous rather large fibrils derived from type I collagen molecules. Fiber-rich scar tissue that ultimately forms contains fibrils predominantly derived from this type of collagen (ibid.). Investigators who have described the fibrillar components involved in wound healing of other tissues have observed type I collagen deposition in fracture healing of bone, both types I and III collagen deposition in the dermis, and type II in cartilage (ibid.). Type IV collagen forms a meshlike scaffold in basement membranes and type V collagen appears to be involved in the migration and movement of capillary endothelial cells during angiogenesis (ibid.).

In a study of controlled epithelial repair in guinea pigs, it was reported that collagen deposition in artificially infected incisions was inhibited by treatment with an acidified chlorite solution (Kenyon, A. J., et al., *Am. Jo Vet Res.* 47:96–101 (1986)). Treated wounds consistently epithelialized rapidly and seldom gaped or exhibited desquamated wound edges, but in the course of healing exhibited less wound breaking strength than control wounds. In the same study, treatment had an antimicrobial effect against *Staphylococcus aureus* experimentally introduced into the wounds.

The overall union of the opposing surfaces of a wound results in an adhering or uniting process referred to as an adhesion. The adhesion may involve tissue formation without differentiation of new elements, resulting in scarring and/or unnatural tissue associations. In surgery, foreign body reactions to lint and starch, serosal damage due to handling, ischemia and tension imposed by suturing and handling, and impaired fibrinolysis can contribute to adhesion formation. Fibrovascular adhesions complicate gynecological, intestinal, tendon, and cardiac surgery (Cohen, et al., cited above, page 576), and may result in ischemia. Adhesion prevention after surgical procedures has been attempted by reducing fibrin deposition using heparin and fibrinolytic agents, inhibiting fibroblast proliferation and collagen deposition using antihistamines or steroids, using careful surgical techniques and separating organs using various techniques, including separation with resorbable fabric. These methods have met with limited success due to the multiple and poorly understood etiology of adhesion formation (ibid.).

In past years, the management of wound treatment and repair was directed to wound healing after surgery or physical trauma. However, certain procedures currently employed in medicine such as those involving indwelling catheters for cleansing or administration of drugs necessitate the routine maintenance of what amount to infection-free wounds. For example, in the treatment of irreversible renal failure (briefly reviewed in Wyngaarden, J. B., et al., *Cecil's Textbook of Medicine,* 19th ed., Harcourt Brace Jovanovich, Philadelphia, 1992, pages 541 to 545), continuous ambulatory or cycling peritoneal dialysis (respectively called C.A.P.D. and C.C.P.D.) are now employed as an alternative to, or an adjunct with, hemodialysis or kidney transplantation. Each year, approximately 1.3 in 10,000 people in the United States develop end-stage renal disease, which is characterized by the accumulation of solutes in the body that can be removed by dialysis, diffusion across a semipermeable membrane down a chemical concentration. Peritoneal dialysis allows for the clearance of larger, and sometimes more toxic, substances than hemodialysis because of the greater permeability of the peritoneal membrane to larger molecules and the longer duration of treatment. Peritoneal dialysis is the dialysis treatment of choice for diabetics and patients with peripheral vascular disease or congestive heart failure because the method provides less cardiovascular stress than hemodialysis, and for children, because they have relatively good peritoneal clearance. Peritoneal dialysis also allows for greater freedom and schedule flexibility and is thus often preferred by working or disabled patients.

In peritoneal dialysis, the dialyzing solution is introduced into and removed from the peritoneal cavity through an abdominal incision. C.A.P.D. makes use of the fact that small molecular weight solutes reach complete equilibration with peritoneal fluid in 4 to 6 hours. Typically, a patient on C.A.P.D. exchanges 1.5 to 3.0 liters of sterile dialysate containing hypertonic glucose and physiologic electrolytes three to five times a day, introduced and removed through a peritoneal dialysis catheter. C.C.P.D. is becoming increasingly popular because the number of daily connects is reduced from four to two by employing the cycler during sleep and a single prolonged, C.A.P.D.-type daytime exchange. Many patients have been managed successfully with peritoneal dialysis for 5 to 10 years, but long-term technique failure rates remain higher than for chronic hemodialysis, mainly because of problems with the peritoneal catheter or recurrent peritonitis (ibid.).

One method almost universally employed for treating wounds of all types, including those surrounding indwelling catheters, is simple cleansing. Surgeons commonly employ mechanical forces to rid wounds of bacteria and other particulate matter retained on wound surfaces. Irrigation can rid wounds of large foreign bodies, but high pressure irrigation is necessary to remove smaller ones, and these can damage tissue and imbed foreign bodies in exposed tissue. Antibiotics added to surgical irrigation solutions appear to provide no additional benefit over saline alone (Hau, T., and Nishikawa, R., *Surg. Gyn. & Obstet.* 156:25–30 (1983)). Disinfectants added to the solutions are potentially toxic; many disinfectants that can be employed on unbroken skin cause tissue damage and damage to tissue defenses when employed on wounds, especially surgical wounds (Cohen, et al., cited above, pages 584–586). Exposure of blood to either Hibiclens® or Betadine® surgical scrub solutions, for example, damage its cellular components. Some surgical irrigants employ a surfactant such as Poloxamer 188 which does not produce discernible toxic effects or allergic reactions in tissues, but this has the disadvantage of exhibiting no antibacterial activity. For wounds that are prone to infection, systemic antibiotic treatment must be employed (ibid.).

It would be advantageous to have a quick-acting, broad-spectrum antimicrobial for use as a surgical irrigant or catheter and wound cleanser that rapidly degrades and does not irritate tissues. It would be especially advantageous to have an antimicrobial that not only does not interfere with wound healing, but, through interaction with the complex processes involved, actually promotes wound healing through a more beneficial route by minimizing scar and adhesion formation.

SUMMARY OF THE INVENTION

It is an object of the invention to provide a method for treating and disinfecting wounds, particularly for the therapeutic and prophylactic treatment of wounds to the peritoneal cavity.

It is another object of the invention to provide a method for disinfecting indwelling catheters and dialyzates of patients undergoing continuous ambulatory or cycling peritoneal dialysis.

These and other objects are accomplished by the present invention, which provides methods for using wound irrigants especially suitable for the peritoneal cavity which may be employed surgically or post-surgically or after physical trauma. The irrigants exhibit broad-spectrum antimicrobial activity, counter inflammation, and minimize scar and adhesion formation during the wound healing process.

The method involves irrigation or infusion of a wound, or catheter cleansing, with a solution containing dissolved chlorine dioxide. The solutions typically comprise from about 0.0005% (5 parts per million, ppm) to about 0.1000% (1000 ppm) of chlorine dioxide ($ClO_2$). One embodiment efficacious in peritoneal dialysis solutions employs from about 5 to about 75 ppm $ClO_2$; another efficacious as a post-surgical irrigant, from about 5 to about 250 ppm $ClO_2$; and a third especially suitable as a surgical irrigant, from about 40 ppm to about 600 ppm $ClO_2$. The chlorine dioxide solutions used in the invention have a relative molar ratio of chlorine dioxide to residual chlorite of at least 5:1, typically at least 7.5:1, and preferably at least 10:1.

The chlorine dioxide solution may be provided in a number of ways. For example, it may be formed immediately prior to infusion or irrigation by combination of a chlorine dioxide liberating compound (such as water-soluble alkali or alkaline earth metal chlorites or mixtures thereof) with a mineral acid such as sulfuric acid, hydrochloric acid, and/or phosphoric acid, followed by adjustment of the pH to about 5 to 7.5. Sodium chlorite is employed in some preferred embodiments.

Alternatively, chlorine dioxide can be formed by reacting a chlorine dioxide liberating compound such as the chlorites mentioned above with an organic acid having a pK of from about 2.8 to about 4.2, such as malic acid, lactic acid, citric acid, mandelic acid, tartaric acid, and mixtures thereof. Lactic acid is employed in one embodiment; organic acids other than lactic acid are employed in other embodiments. Chloride ion can optionally be used in these formulations, as can carbohydrate triggering substances that accelerate the formation of chlorine dioxide.

Alternatively, chlorine dioxide can be formed by reacting a chlorine dioxide liberating compound, such as the chlorites mentioned above, with a saccharide which has been heat-activated by heating the saccharide to a temperature of from about 50° C. to about 150° C. for at least about 1 minute, typically from about 5 to 240 minutes and preferably from about 20 to 120 minutes, in a solution in the presence of an organic acid having a pK of about 2.8 to about 4.2 and at a pH below about 5.5. Typical saccharides used in these formulations include glucose, galactose, mannose, ribose, rhamnose, lactose, sucrose, maltose, and mixtures thereof.

The volume of chlorine dioxide-containing solution used as a wound irrigant according to the method of the invention varies with the size of the wound and the mammal and the scope of the infection or potential infection, and can range between about 10 milliliters to about 5 liters.

Solutions employed for wound irrigation according to the method of the invention typically contain a pharmaceutically acceptable carrier. Pharmaceutically acceptable carriers include any that do not irritate the wound or cavity, including dialysis solutions and isotonic solutions containing saline and other inorganic (e.g., phosphates and sulfates) and organic salts. Typical solutions have a pH of from about 5 to 7.5. The solutions may optionally contain suitable wetting agents and emollients.

DETAILED DESCRIPTION OF THE INVENTION

This invention is based upon the finding that a solution containing chlorine dioxide having defined chlorine dioxide-to-chlorite molar ratios that limit tissue irritation are efficacious as wound irrigants both prophylactically and therapeutically.

In one embodiment, the present invention is directed to the use of effective amounts of chlorine dioxide as a peritoneal cavity irrigant. The enteric organisms which enter the peritoneal cavity through contamination by gastrointestinal contact, whether by physical trauma or during surgery, are all susceptible to the cidal effects of chlorine dioxide, which is a broad-spectrum antimicrobial. Chlorine dioxide has demonstrated activity against all relevant organisms, both aerobic and anaerobic, including lactobacilli, streptococci, coliforms, *Klebsiella* species, *Enterobacter* species, *Bacteroides* species, clostridia and eubacteria. Irrigation of the peritoneal cavity with saline, in concert with systemic antibiotic therapy, has been found to be beneficial in the treatment of peritonitis. However, as mentioned in the Introduction, addition of antibiotics to the irrigating solution has not provided any additional benefit (Hau and Nishikawa, cited above), and it is presumed that the peritoneal irrigation derives from its mechanical effect. The ineffectivenss of local antibiotic solutions has been surprising to researchers, since the antibiotics that have been used were capable of in vitro inhibition of the bacterial species present in the peritoneal cavity. It may be that the lack of effect was attributable to the brevity of contact of the antibiotic with the organisms, since usual flush times approximate five minutes or less in duration, which would be too short for significant cidal action to occur.

This invention provides a quick-acting, broad-spectrum antimicrobial, that is not absorbed systemically because it is rapidly eliminated or degraded. The inventive compositions have the requisite, extended range of antimicrobial action, rapidity of kill and degradability for this application. For example, 50 ppm $ClO_2$ solutions have been shown to kill 6-logs/ml of a wide variety of organisms within one minute, including *Pseudomonas aeruginosa, Staphylococcus* species, *Escherichia coli* and other coliforms, *Klebsiella pneumoniae, Streptococcus* species, and *Bacteroides* species. $ClO_2$ reacts with oxidizable bonds of these organisms and other organic matter and, as a result, is reduced to lower oxidation states: initially chlorite and ultimately chloride. The latter is present at high levels in the body (ca. 0.5% of cellular fluids), so that the small amount formed by $ClO_2$ degradation (in the parts per million range) would disappear into that pool. Compatability of these disinfecting peritoneal flush solutions is also appropriate, since the $ClO_2$ is generated or dissolved in solutions which have osmotic pressures that are suitably isotonic with cellular fluids.

As has been mentioned, the inflammatory process resulting from bacterial infection of wounds in the peritoneal cavity, e.g., peritonitis, can, upon treatment, either resolve with no residual effects or can lead to the formation of scarring and/or fibrous adhesions. An additional feature of $ClO_2$ and related oxychlorine systems is their capability to inhibit the stimulation of fibroplasia, the proliferation of fibroblast cells and expression of collagen, which ordinarily ensues following wounding. As shown in the examples that follow, the oxychlorines resulting from acidification of chlorite to form chlorous acid significantly inhibits fibroblast proliferation and collagen formation.

A further study confirming the effect of $ClO_2$ on wound healing set out in greater particularity below combines an investigation of the immediate cellular response (chemotaxis) of the body to injury using isolated polymorphonuclear leukocytes, and another investigation assessing the interaction of $ClO_2$ with free radicals which form during the course of tissue repair collagen synthesis. In the former case, $ClO_2$ was found to control chemotaxis by affecting the quality and morphology of the associated polymorphonuclear leukocytes. In the latter case, the $ClO_2$, which is a stable free radical containing one unpaired electron, was found to neutralize the superoxide and related radicals involved in the process of collagen production.

In another embodiment, this invention is directed to the use of oxychlorines as a prophylactic or therapeutic rinse for individuals on peritoneal dialysis. Over 100,000 persons in the United States require dialysis treatments to supplement or replace the activity of failing or failed kidneys. The majority of these people rely on hemodialysis, which involves several hour sessions, three times per week, during which time their blood is passed through an external hemodialysis apparatus. As discussed in the Introduction, an alternative treatment is Continuous Ambulatory or Cycling Peritoneal Dialysis (C.A.P.D. and C.C.P.D.), where their peritoneal cavities are filled with phosphate-buffered sugar solution, and the peritoneal membrane acts as a dialyzing filter for waste products that have accumulated in the blood. This technique frees the patient from thrice-weekly immobilization on a dialysis machine, but has a tendency to promote peritoneal infections in the cavity by transfer of skin organisms into the peritoneum when the indwelling catheter that delivers the fluid is inserted. Other transfer of organisms takes place when connecting the daily dialysis fluid supply. Once an organism has reached the cavity, typically *Staphylococcus epidermidis*, it deposits on the catheter surface and grows a protective glycocalyx structure around its colonies. As a result, the average C.A.P.D. or C.C.P.D. patient has a peritonitis infection at least once a year, which dissuades many people from this otherwise less-encumbering dialysis procedure. This invention, which is efficacious in the destruction of *S. epidermidis* encased in biofilms as illustrated below, provides a method to reduce this incidence.

The $ClO_2$-containing isotonic solutions of the invention can be used for C.A.P.D. patients in one of two ways. It can be included in the daily volume of the dialyzate infused into the patient, as a prophylactic means of destroying any incidental organisms that might be transferred during the daily exchange of fresh fluid for spent dialyzate. In this situation, a separate satellite bag of $ClO_2$ solution can be transferred to the main dialyzate volume prior to introduction into the peritoneum. The satellite bag itself can be a dual container of components which, when mixed, would release $ClO_2$ at an appropriate level such that its dilution in the dialyzate fluid would approximate the desired final concentration (e.g., 5 to 75 ppm).

In another application, the method of the invention is employed to treat peritonitis in C.A.P.D. patients which arises from penetration of organisms into the peritoneum. While free-floating organisms are susceptible to the cidal effects of $ClO_2$, *S. epidermidis* colonies on indwelling catheters can also be effectively destroyed. These colonies intermittently recontaminate the peritoneal cavity, which may be subsequently treated with an antibiotic without destroying the protected colony on the catheter surface. As set out in the examples hereinafter, the cidal effectiveness of $ClO_2$ was demonstrated using *S. epidermidis* biofilms that were grown on flat plates and exposed to a variety of disinfectants and antibiotics.

The method of the invention can also be used post-surgically. Following surgery, particularly abdominal surgery, it is generally necessary to flush the area of the operation with sterile saline solution to remove organic debris, including blood and serious fluids. When the surgery involves the gastrointestinal tract, there is generally the added presence of those organisms which inhabit that system. Even without such involvement, organisms in the surgical environment, although much reduced from normal levels, can deposit on the site, and must be removed. Without such removal, serious infections can result after closure of the incision or wound. It is desirable therefore to incorporate an antimicrobial material in the flush, but broad use of antibiotics is discouraged and use of antiseptics such as hypochlorite or peroxide is discouraged because of tissue incompatibility at levels that might be considered effective.

It is an advantage of the invention that solutions containing fairly significant levels of $ClO_2$ are particularly well tolerated by tissues. For example, solutions of 350 ppm in buffered saline have been shown to be safely infusable into cows' udders without stimulation of any immune response by the animals. $ClO_2$ is capable of being reduced to lower oxidation states, such as chlorite and chloride, upon contact with organic materials, but is less reactive than, for example, hypochlorite, and a volume of $ClO_2$-containing saline is expected to retain significant antimicrobial activity when used to flush out organic debris from an incised area. Appropriate use levels of $ClO_2$ will vary, depending on the amount of organic detritus in the site, but generally concentrations of about 5 to 250 ppm in approximately isotonic solution can be used with good effect.

It is a further advantage of the invention that $ClO_2$ is a broad-spectrum antimicrobial, capable of rapid destruction of aerobic and non-aerobic, gram-positive and gram-negative bacteria, as well as fungal organisms and viruses. It is particularly suitable for inclusion in a surgical irrigant or flush, since there is a diversity of microorganisms that could contact exposed areas during surgical procedures. The unique benefit of $ClO_2$, in addition to its high cidal capacity, is its ability to interfere with the biochemical processes that lead to augmented collagen production. As such, it can significantly suppress undesirable adhesions that often form between incised tissues during the course of post-surgical healing.

The method of the invention employs the broad-spectrum antimicrobial, chlorine dioxide ($ClO_2$), typically provided from chlorine-dioxide generating compounds, in solution for body cavity, catheter, and wound disinfection. Preformed chlorine dioxide is too unstable to be stored in neutral disinfectant solutions for any significant period of time. The methods of the invention can be employed as a treatment for peritonitis, as a prophylactic or therapeutic rinse for people undergoing peritoneal dialysis, as a surgical irrigant, and as a disinfecting ear flush.

In contrast to antibiotics, systemic absorption of the compositions of the invention is minimized in treatments using them because of the inorganic nature of chlorine dioxide, and its reductive degradation to chloride as a result of its interaction with organic matter (including bacteria, fungi, and viruses). It is important to note that materials may be non-inflammatory (i.e., not provoke inflammation) but not anti-inflammatory (i.e., counter the effects of inflammation). Chlorine dioxide has been found to be non-inflammatory, by virtue of being infusible into the peritoneal cavity and other body cavities without evoking the inflammatory response, as well as being anti-inflammatory; see the copending U.S. application Ser. No. 08/133,465, filed Oct. 8, 1993, and parent case U.S. Pat. No. 5,252,343, cited and incorporated by reference above. In order to utilize the germ-killing and non-inflammatory qualities of chlorine dioxide, it is preferable to isolate it from chlorites and its acidic form, chlorous acid (which have detrimental cytotic effects).

To minimize the negative effects caused by chlorite (and chlorous acid in lower pH solutions), techniques are employed which preferably either a) deliver the soluble chlorine dioxide gas in a solution relatively free of harmful chlorite, or b) employ a pre-infusion chemical reaction whereby the chlorite species has substantially converted to chlorine dioxide leaving relatively little chlorite remaining. In both cases, the relative molar ratio of chlorine dioxide to residual chlorite is at least 5:1, typically at least 7.5:1, and preferably at least 10:1. The concentration of chlorine dioxide in the infusate or irrigant typically varies from about 5 ppm (mg/liter) to about 1000 ppm in most embodiments, and is generally at least about 10 ppm. One embodiment employs from about 5 to about 75 ppm $ClO_2$; as mentioned above, this is especially efficacious in peritoneal dialysis solutions. Another employs from about 5 to about 250 ppm $ClO_2$; this is especially suitable as a post-surgical irrigant. A third particularly useful as a surgical irrigant employs from about 40 to about 600 ppm $ClO_2$.

As addressed below, the concentration requirement depends, to a significant degree, on the type of use for which the solution is employed, and the total volume used, since it is the total quantity of chlorine dioxide (i.e., concentration times volume) that is critical to the goal of overcoming the neutralizing effects of organic matter in the wound in order to achieve the antimicrobial and beneficial healing effects of chlorine dioxide.

Any means may be used for the preparation of a chlorine dioxide composition for use in the method of the invention. In many embodiments, a chlorine dioxide generating compound is reacted with an acid in an aqueous solution. Exemplary chlorine dioxide generating compounds are water-soluble chlorites such as alkali metal chlorites, alkaline earth metal chlorites, and mixtures of these. Sodium chlorite is employed in preferred embodiments.

In conventional means of producing chlorine dioxide solutions, a mineral acid is reacted with a chlorite such as sodium chlorite at such concentrations as to provide rapid evolution of chlorine dioxide. Typical mineral acids include, but are not limited to, sulfuric acid, hydrochloric acid, phosphoric acid, and the like. Such admixture, however, results in a very acidic solution that requires neutralization before use. Typical solutions are neutralized to a pH of from about 5 to about 7.5 prior to use.

Alternatively, a chlorine dioxide generating compound such as the chlorites mentioned above can be reacted with a weaker acid, such as an organic acid having a pK of from about 2.8 to about 4.2. Typical acids include lactic acid, citric acid, malic acid, glycolic acid, mandelic acid, tartaric acid, and mixtures thereof. One embodiment employs lactic acid; the lactate so formed may enhance angiogenesis, collagen synthesis and deposition, and modulate the response of fibroblasts to growth factors in the wound as summarized by Ninikowski, J., et al., in Janssen, H., et al., eds., *Wound Healing*, Wrightson Biomedical Publishing Ltd, Petersfield, U.K., 1991, pages 169 to 170. In embodiments where these effects are not desired, organic acids other than lactic acid are employed.

The preparation of these types of formulations is set out in U.S. Pat. No. 4,986,990 to Davidson and Kross, the disclosure of which is hereby incorporated herein in its entirety by reference. In that patent, concentrations of sodium chlorite and activating acid are both below about 0.01–0.02%, in isotonic saline. Such solutions have been found to be appropriate for use in the uterine infusion treatment of the present invention for chlorine dioxide levels up to about 125 ppm. The solutions may require pH adjustment, e.g., to about 5 to about 7.5. The reactions, upon admixture, are virtually complete within several minutes, and can generate chlorine dioxide solutions in excess of 40 ppm with solution pH's compatible with the peritoneal cavity. When higher levels of chlorine dioxide are required, stronger acids and higher levels of chlorite may be used, with subsequent neutralization prior to infusion. Typical solutions can contain up to about 1000 ppm chlorine dioxide, but higher concentrations, e.g., up to about 5000 ppm chlorine dioxide are employed in some embodiments.

The inclusion of small amounts of certain activating sugars (e.g., ribose, galactose, mannose) in the formulation, for example, at levels at or below about 1%, can further increase the speed and efficiency of chlorine dioxide formation. It has been found that this reaction, with or without the addition of sugar triggers, can provide the requisite chlorine dioxide-to-chlorite molar ratios of at least 5:1 that are necessary to limit tissue irritation.

The composition may contain chloride ion, which is typically in the form of an alkali or alkaline earth metal salt. For sodium chloride, for example, concentrations can range between about 0.5% to 1.5% by weight; use of other salts requires an appropriate weight percent adjustment. In solutions below pH about 7, chloride ion causes chlorite ion to decompose in an accelerated manner, via the degradation of chlorous acid to form chlorine dioxide. Preferred embodiments of the invention employ solutions that are approximately isotonic to the peritoneal cavity or peritoneal dialysis solutions.

In another embodiment, chlorine dioxide formation in the reaction between chlorite and weaker acids is catalyzed by heat-activated saccharides. Heat-activated saccharides are prepared by heating saccharides to a temperature of from about 50° C. to about 150° C. for at least about 1 minute, typically from about 5 to 240 minutes. Some heat-activated saccharides are prepared by heating to about 75° C. to about 110° C. for about 20 to 120 minutes. Exemplary saccharides include, but are not limited to, glucose, galactose, mannose, ribose, rhamnose, and disaccharides such as sucrose, lactose, and maltose, and mixtures thereof. Glucose is preferred in one embodiment. Heat-activated saccharides useful in these embodiments of the invention are described in greater detail in U.S. Pat. No. 5,019,402 to Kross and Scheer, the disclosure of which is hereby incorporated herein in its entirety by reference.

The chlorine dioxide solutions are generally buffered mixtures that maintain the irrigant at a pH compatible with the peritoneal or other cavity. The pH typically varies between about 4.5 or 5.0 and about 7.5. The solutions can contain other ingredients typical in washes and irrigants such as, for example, wetting agents (such as nonylphenoxy polyoxyethylene (9)), soothing emollients, and the like. Suitable carriers are chosen for their ability to dissolve or disperse chlorine dioxide as well as provide a composition conducive to infusion or irrigation. Many such compositions are known in the art, and can include thickening and emulsifying agents and the like, and such carriers are referred to herein as pharmacologically acceptable carriers.

The solutions may be prepared immediately before infusion or irrigation in one embodiment. In another embodiment, the chlorine dioxide solution may be prepared and stored below a pH of about 5.5. For more particulars about storage, including storage of components and mixing of these prior to use, reference is made to U.S. Pat. Nos. 4,986,990 and 5,019,402, cited above, and references cited therein. Briefly stated, for the delivery of preformed aqueous chlorine dioxide, the following criteria should be met: 1) a storage pH below about 5.5 to minimize the degradation of chlorine dioxide to chlorite and other species; 2) a concentration of sodium chloride or equivalent material sufficient to render the solution approximately isotonic (e.g., from about 0.80 to about 1.0% NaCl); 3) a package container that is virtually impermeable to, and non-reactive with, chlorine dioxide, such as glass and certain grades of polyacrylonitrile and polyvinylidene chloride. Immediately before the infusion or irrigation, a suitable buffer is typically added to these solutions. Formulations for particular applications such as use in peritoneal dialysis and catheter cleansing are discussed more fully below.

The volume of infusates varies with the size of the animal and the degree of infection or potential infection, and can range between about 10 milliliters to about 5 liters. Example volumes are given hereinafter.

When solutions of the invention are infused into the peritoneal cavity, they are well tolerated, producing no noticeable irritation effects in the animals tested. Infusions with solutions of the invention are especially efficacious in the treatment of peritonitis.

Another important feature associated with the use of chlorine dioxide infusions or irrigations for the control of peritonitis and related disorders is its fairly rapid reduction to chloride ion, which is a common component of body fluids and tissues in general. This reduction occurs by interaction with organic matter, including bacteria. Topical agents that are non-toxic to cells without systemic absorption are especially needed for the destruction of potentially resistant isolates and for the treatment of dialysis patients who have recurrent infections.

Since a sufficient excess of the chlorine dioxide provides microbiocidal activity at a more rapid rate than the rate of depletion of the molecule's oxidizing power by the organic environment, some antimicrobial efficacy may be achieved from the chlorine dioxide despite its rapid reduction by organic matter. Thus, a chlorine dioxide infusion into the peritoneal cavity which may contain significant amounts of organic material (e.g., mucus, serum, and sloughed cells) can still provide antimicrobial activity.

Both reduction of wound organic matter with the chlorine dioxide and longer contact time increase the antimicrobial effectiveness of the chlorine dioxide solution. These data suggest that the infusion of a sufficient volume of a chlorine dioxide solution into a wound such as a peritoneal cavity wound, to overcome residual quantities of materials present during infection, could destroy microorganisms present in the environment. In some embodiments, volumes of 1 to 4 liters are employed in repeated irrigations during surgery. Higher chlorine dioxide concentrations in these volumes would similarly enhance the cidal activity, and are particularly advantageous in the cleansing of catheters. Since residence times of such infusions can be lengthened, there would be ample time for the antimicrobial to operate before being chemically neutralized.

The ability of the chlorine dioxide solutions to bring about a marked reduction in *Staphylococcus epidermidis* biofilms frequently observed on the surface of C.A.P.D. and C.C.P.D. catheters described in greater particularity below is significant. Also significant are studies illustrating the ability of oxychlorines to minimize collagen formation (noted by Kenyon, et al., cited above, in epidermal tissue, who reported a 50% drop in collagen formation), and scavenge free radicals involved in wound repair as set out below. Thus, irrigation of wounds with combined lactic acid and chlorite solutions significantly provides not only disinfection, but promotes healing and epithelization by minimizing collagenous scar formation.

Use of the chlorine dioxide solutions of this invention, with their rapid degradation to chloride salts, further allows for their application as a prophylactic treatment, which is especially useful in irrigation of surgical sites, peritoneal cavity surgery, and in the cleaning of indwelling peritoneal catheters. Infusion or irrigation with chlorine dioxide solutions could significantly reduce the impact of microbial invasion of the peritoneum.

EXAMPLES

The following examples are presented to further illustrate and explain the present invention and should not be taken as limiting in any regard. Unless otherwise indicated, all parts and percentages are by weight, and are given for the particular processing step described.

EXAMPLE 1

This example compares and contrasts the cidal effectiveness of compositions of the invention with other disinfectants and antibiotics against *Staphylococcus epidermidis* biofilms, which are frequently observed on the surface of C.A.P.D. peritoneal catheters even in the absence of peritonitis or exit site infections.

A strain of *S. epidermidis* with characteristic abundant slime production, and derived from a human source, is used to prepare the biofilms. The isolate is fully sensitive in the fluid phase to all commonly used antibiotics as assayed using routine test methods. Aliquots of the bacteria are frozen at −70° C. in 10% glycerol broth or propagated on 5% defibrinated horse blood agar. Standardized biofilms are formed on soda glass microscope slides or slides coated with Silastic® (the basic material of indwelling catheters; see Cecil's, cited above, on page 542), placed in Petri dishes containing 20 ml of tryptone soya broth (Oxoid Ltd., England), seeded with $10^4$ cfu *S. epidermidis* and incubated for 18 hours at 37° C. Reproducible uniform and confluent *S. epidermidis* biofilms of minimal density are formed.

Antibiotic activity against *S. epidermidis* biofilms are determined using a supravital dye which acts as an electron acceptor in coupled oxidative systems in biofilm bacteria. The method allows the bacteria to be examined undisturbed within the biofilm matrix in situ. Briefly stated, the biofilms are exposed to antibiotic solutions and incubated at 37° C. for varying periods of time. Positive (viable, 1% peptone water) and negative (sterilized, 4% formol-peptone) controls are included in all experiments. After a designated exposure at 22° C. for varying periods of time between 15 seconds to 6 hours, the biofilms are rinsed twice in sterile water and allowed to drain. They are then placed in a flat agar medium incorporating substantive dyes and incubated at 37° C. for 4 hours, then 24 hours. Viability is assessed visually by a change in dye color and confirmed after 24 hours by mechanically scraping and subsequently culturing the biofilms. Sterilization is indicated by the absence of color changes and confirmed by culture of both intact and mechanically fragmented biofilms. Inhibition of growth is indicated by a lack of color change after a 4-hour incubation and confirmed by a positive color change by 24 hours.

Using this technique, the following results are obtained:

| Test Formulation | Exposure Time (22° C.) for Film Sterilization |
| --- | --- |
| 50 ppm $ClO_2$ Solution | 5 seconds |
| Dakin's Solution (0.5% Hypochlorite) | 5 seconds |
| Povidone-Iodine (10%) | 5 seconds |
| Hydrogen Peroxide (3%) | 10 minutes |
| 4% Formaldehyde/Saline | 3 hours |
| Rifambin (100 μg/ml) | 6 hours |
| 38 Other Antibiotics* | >24 hours |

*None of the following antibiotics showed any activity against the bacteria after a 24 hour exposure to concentrations shown in parenthesis: amikacin (60 μg/ml), ampicillin (30 μg/ml), bacitracin (20 μg/ml), Bactrim ® (25 μg/ml), cefadroxil (30 μg/ml), cefamandole (60 μg/ml), cefazolin (30 μg/ml), cefoperazone (30 μg/ml), cefotaxime (30 μg/ml), cefsulodin (30 μg/ml), ceftazidime (30 μg/ml), cefuroxime (30 μg/ml), cephalexin (30 μg/ml), chloramphenicol (20 μg/ml), ciprofloxacin (12.5 μg/ml), clindamycin (20 μg/ml), cloxacillin (20 μg/ml), erythromycin 45 μg/ml), fusidic acid (30 μg/ml), gentamicin (30 μg/ml), imipenem (20 μg/ml), moxalactam (30 μg/ml), neomycin (30 μg/ml), norfloxacin (20 μg/ml), novobiocin (60 μg/ml), oleandomycin (45 μg/ml), penicillin G (25 μg/ml), rifampin and clindamycin or rifampin and gentamicin or rifampin and tetracycline (at concentrations of 20 μg/ml rifampin and 10 μg/ml other antibiotic), spectinomycin (20 μg/ml), streptomycin (20 μg/ml), subactam and ampicillin (20 μg/ml each), tetracycline (60 μg/ml), tobramycin (20 μg/ml), trimethoprim-sulfamethoxazole, and vancomycin (60 μg/ml).

The materials in the table which are as effective as the 50 ppm $ClO_2$ solution are ones that would be considered to be too irritating and/or corrosive for use as an irrigant in a peritoneal cavity. The 50 ppm $ClO_2$ solution, on the other hand, is well tolerated by mammalian tissue, as, for example, when used as an eye irrigant, to treat bacterial infections induced in rabbits, to infuse into a cow's udder, or as a uterine douche for mares and cows in the prevention and treatment of endometritis.

Moreover, the 0.5% hypochlorite will also be subject to significant loss of activity as a result of its interaction with organic materials in peritoneal fluid. Hydrogen peroxide, at a concentration of 3%, requires a contact time 1200 times longer than the 50 ppm $ClO_2$ to destroy the organisms in the biofilm, and also is likely to be too corrosive for infusion into the peritoneum. The 4% formaldehyde/saline solution is similarly inappropriate for such treatment, and would take more than 2000 times longer for sterilization. The best antibiotic of those tested, rifampin (Rimactane®, obtained from Ciba-Geigy), took 6 hours to accomplish the same sterilization. Thus, the use of an isotonic $ClO_2$ solution for eliminating the focal point of recurring peritoneal infections in patients undergoing Continuous Ambulatory Peritoneal Dialysis (C.A.P.D.) or Continuous Cycling Peritoneal Dialysis (C.C.P.D.) is particularly appropriate.

This conclusion is underscored in studies that assess the efficacy of methods employed using compositions of the invention in combination with an infusate used in C A P D and C C P D practice, Inpersol® Abbott Laboratories, Montreal, Canada, which contains 4.25% dextrose and has a pH of 5.2. A 50 ppm $ClO_2$ solution is diluted from 1:2 to 1:10 with normal saline (denoted below as NS), Inpersol® peritoneal dialyzate (denoted as PD), and peptone-saline (a standardized protein digest obtained from Oxoid, denoted as PS). Four percent formol saline, a known potent environmental disinfectant of considerable toxicity, is used as a reference. The results are expressed as the minimal time of exposure at 22° C. to effect sterilization of *S. epidermidis* biofilms:

| | 50 ppm $ClO_2$ | | | Formol Saline | | |
|---|---|---|---|---|---|---|
| Dilution | NS | PD | PS | NS | PD | PS |
| 1/2 | 15 sec | 5 sec | 1 min | 8 hr | 6 hr | 8 hr |
| 1/3 | 30 sec | 1 min | 3 min | 12 hr | 6 hr | 12 hr |
| 1/5 | 5 min | 5 min | 1 hr | 18 hr | 24 hr | 24 hr |
| 1/7 | 15 min | 7 min | 4 hr | 24 hr | 24 hr | >24 hr |
| 1/10 | 1 hr | 10 min | 24 hr | 24 hr | 24 hr | >24 hr |

It can be seen that though diluting with the peptone solutions has an inhibitory effect on the sterilizing activity of $ClO_2$ solution, the peritoneal dialysis solution markedly enhances antimicrobial activity of the $ClO_2$ solution.

EXAMPLE 2

To test whether methods of the invention can control the inflammatory response, isolated polymorphonuclear leukocytes, which are among the first cells to be found at a wound or a site of potential infection, are studied with respect to their response to chlorine dioxide solutions and compared with a control containing ibuprofen, a known non-steroid anti-inflammatory compound. The choice of in vitro assay is chemotaxis.

Isolated polymorphonuclear leukocytes are studied with respect to their response to a $ClO_2$ solution varying in concentration from 3 to 300 ppm and an ibuprofen control. Cellular response and integrity (chemotaxis) is assayed in vitro after incubating with both compounds by measuring lactate dehydrogenase activity and/or release concurrently with observing morphology using scanning electron microscopy and/or transmission electron microscopy.

Figure 1:
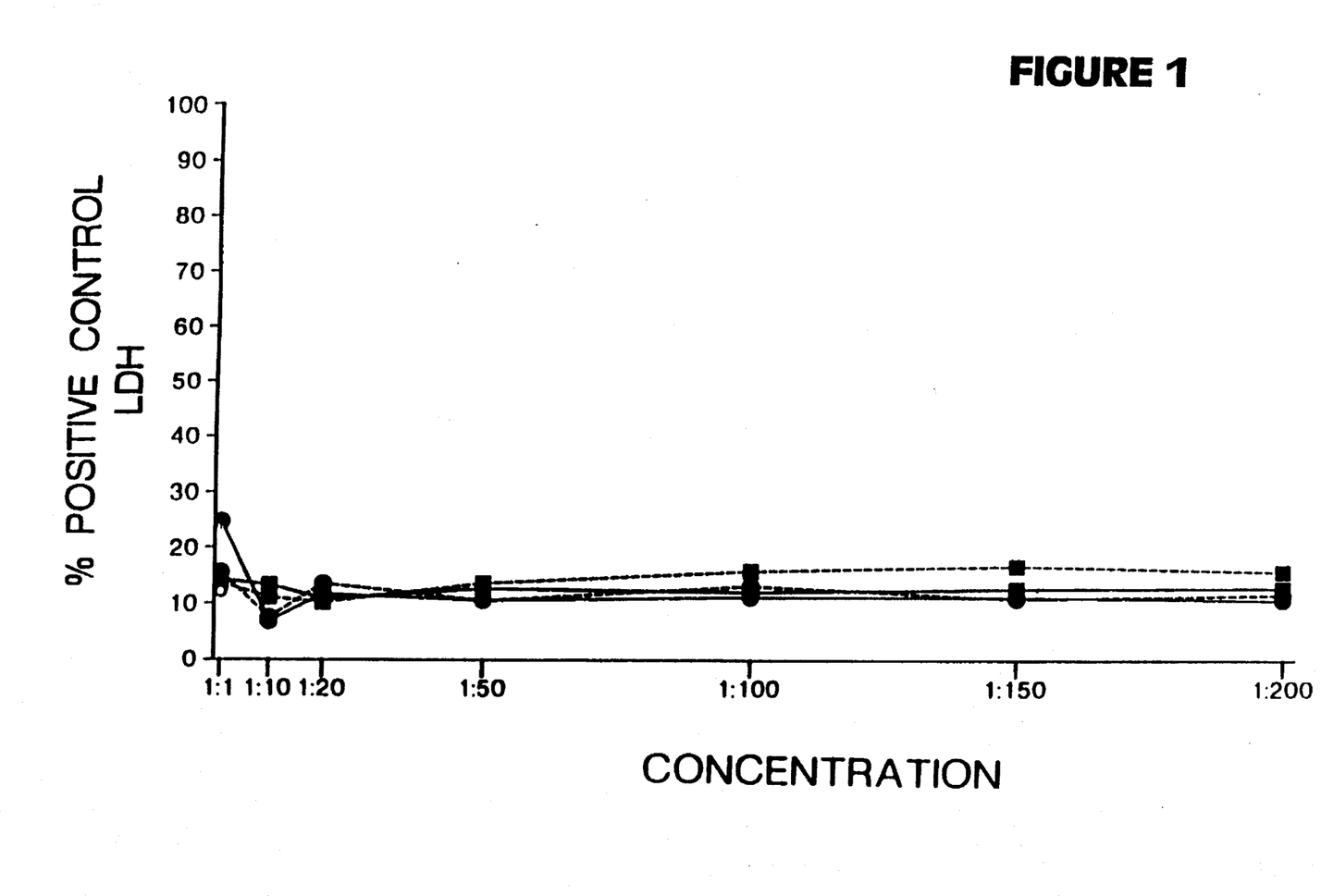
FIG. 1 is a graphical plot of data obtained in lactate dehydrogenase assays of isolated polymorphonuclear leukocytes in the presence of chlorine dioxide solutions used according to the method of the invention and antiinflammatory ibuprofen controls. The figure plots lactate dehydrogenase activity, expressed as % of a positive control, versus dilutions of chlorine dioxide solutions (●) or ibuprofen (■), and shows the effect of chlorine dioxide or ibuprofen on cell integrity with (solid lines) or without (dashed lines) incubating with 0.05% bovine serum albumin (BSA) prior to the assay. A negative control is denoted by o.
Figure 2:
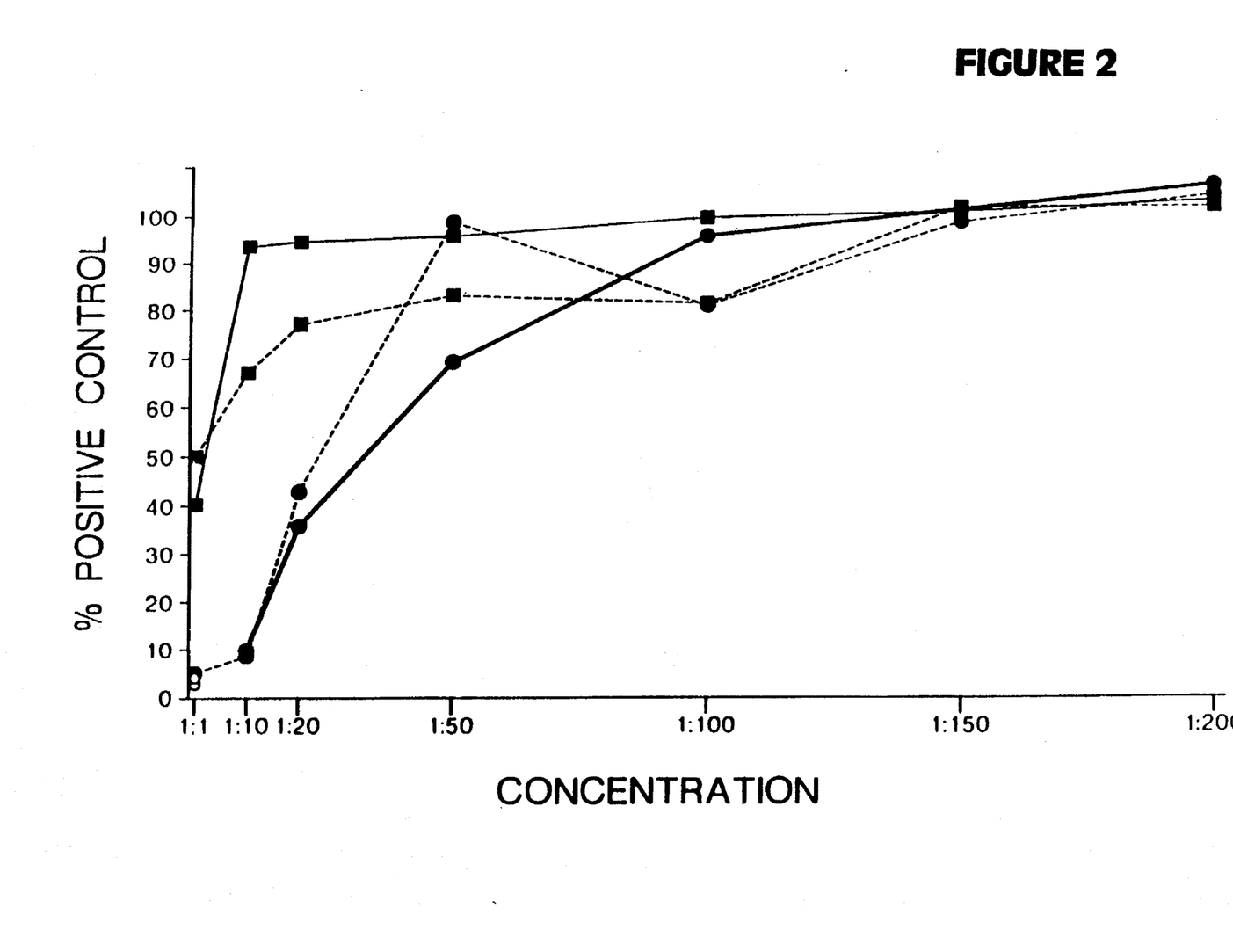
FIG. 2 is a graphical plot of data collected using chlorine dioxide and ibuprofen at various dilution levels run concurrently in a chemotaxis assay employing 10% bovine serum albumin with polymorphonuclear leukocyte cells. In the figure, ●—● and ●——● show the chlorine dioxide results, ■—■ and ■——■ show ibuprofen results, and o is a negative control.
Figure 3:
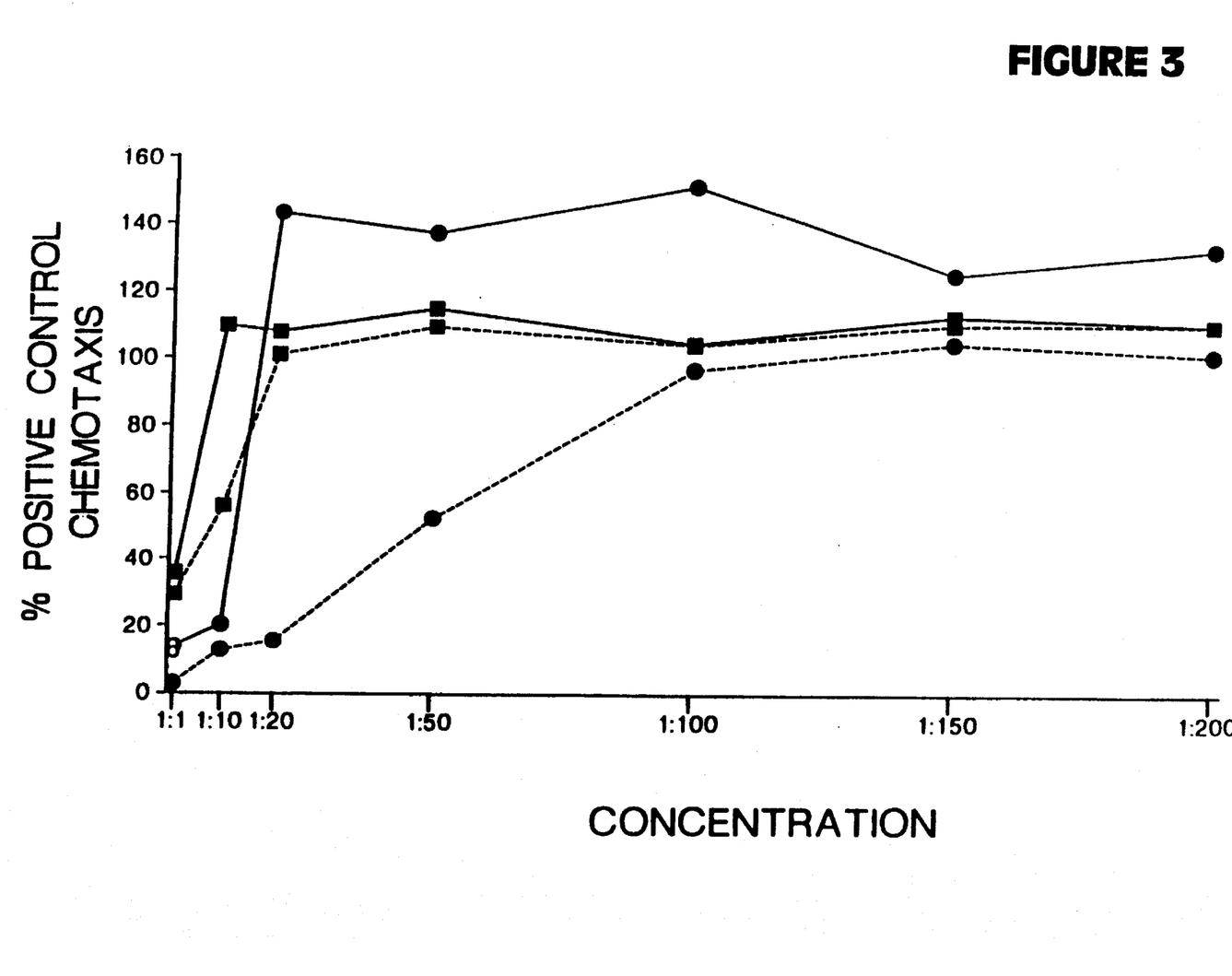
FIG. 3 shows the results of a polymorphonuclear leukocyte chemotaxis assay that employs chlorine dioxide (●) and ibuprofen (■) at various dilution levels and bovine serum albumin levels of 0.05%. In the figure, the solid lines represent data obtained after incubation of the solutions with bovine serum albumin prior to addition of cells, and the dashed lines represent incubation of the cells with the solutions prior to addition of bovine serum albumin. A negative control is shown as o.

The results are graphically illustrated in FIGS. 1 to 3. The x-axis in the figures show dilutions of a 0.5 mg/ml ibuprofen solution, and chlorine dioxide solutions prepared by combining lactic acid with sodium chlorite and diluting to yield chlorine dioxide concentrations as follows: 1:1 is 300 ppm $ClO_2$, 1:10 is 60 ppm $ClO_2$, 1:20 is 30 ppm $ClO_2$, 1:50 is 12 ppm $ClO_2$, 1:100 is 6 ppm $ClO_2$, 1:150 is 4 ppm $ClO_2$, and 1:200 is 3 ppm $ClO_2$.

FIG. 1 shows the data obtained from the lactate dehydrogenase assays. The figure plots lactate dehydrogenase activity, expressed as % of a positive control, versus dilutions of chlorine dioxide solutions or ibuprofen, and shows the effect of chlorine dioxide or ibuprofen on cell integrity with or without incubating with 0.05% bovine serum albumin (BSA). In the figure, ●—● shows the results of incubating chlorine dioxide and BSA for 15 minutes, adding cells, centrifuging and then assaying the supernatant, and ●———● plots data obtained by incubating chlorine dioxide and cells for 15 minutes and then adding BSA, centrifuging and assaying the supernatant. For comparison, ■—■ shows ibuprofen incubated with BSA for 15 minutes, followed by adding cells, centrifuging and assaying, and ●———●, incubation with cells for 15 minutes followed by adding BSA, centrifuging and assaying. A negative control is denoted by o.

FIG. 2 shows chemotaxis when chlorine dioxide and ibuprofen are run concurrently in a chemotaxis assay. The figure shows the effect of 0.10% bovine serum albumin on the cells. The albumin is added to the cells and incubated 15 minutes, and then cells are mixed in equal volumes with dilutions of chlorine dioxide or ibuprofen and incubated; 250 µl of each mixture is then applied to the top well of a modified Boyden chamber. The y-axis plots percent of a positive control. In the figure, ●—● and ●———● show the chlorine dioxide results, ■—■ and ■———■ show ibuprofen results, and o is a negative control.

FIG. 3 shows the results of the chemotaxis assay. It demonstrates the effect of the difference in the sequence in which reagents are added and incubated. In one experiment, for each dilution, there is a known volume of chlorine dioxide (●———●) or ibuprofen (■—■) to which bovine serum albumin is added to a final concentration of 0.05%, the mixture is incubated for 15 minutes, and equal volumes of cells are added to each to a final concentration of $2.5 \times 10^6$ cells/mi. In a second experiment, for each dilution, a known volume of cells containing approximately $6.0 \times 10^6$ cells/ml and an equal volume of chlorine dioxide (●———●) or ibuprofen (■———■) are incubated for 15 minutes and then bovine serum albumin is added to a final concentration of 0.05%. In each assay, 250 µl is applied to the top well of a modifed Boyden chamber. A negative control is shown as o.

It can be seen that the $ClO_2$ solution affected both the quality and morphology of polymorphonuclear leukocytes.

EXAMPLE 3

Since recent studies indicate that the superoxide radical is the active form of oxygen in the prolyl and lysyl hydrolyase reactions during collagen synthesis, this example assesses the effects that compositions of the invention have on free radicals.

Free radicals are generated in vitro by the action of xanthine oxidase (XO) on xanthine. The generation of free radicals is monitored by the reduction of ferricytochrome C by the system. The action of chlorine dioxide is compared with the scavenging action of the well known free radical scavengers superoxide dismutase (SOD) and catalase.

ClO$_2$ (75 ppm) is generated by mixing 0.25% chlorite and 1.4% lactic acid. One hundred-fold dilutions are tested within one minute after mixing using electron paramagnetic spectroscopy (ESR) and a LKB luminometer. A strong free radical signal is generated using both methods, and the signal is quenched using the free radical scavengers.

For the ESR assay, the chlorine dioxide solution is frozen in liquid nitrogen to −167° C. and electron spin resonance analyzed using a Varian E3 instrument.

The luminometer assay utilizes a modified luminol assay for radical detection. Luminol (LH$_2$) reacts with free radicals (R·) as follows:

$$LH_2 + R\cdot \rightarrow LH\cdot$$

$$LH\cdot + O_2 \rightarrow LOO^- \text{ (endoperoxide)}$$

$$LOO^- \rightarrow L_2 + AP^* \text{ (aminophthalate dianion, active state)}$$

$$AP^* \rightarrow AP \text{ (inactive)} + h\nu$$

The pH optimum for the reaction is 10 to 12. The assay is standardized with an enzymatic system in which the generation of free radicals could be quantified by measuring generation of ·O$_2^-$, obtained with the following reaction, hypoxanthine+xanthine oxidase→urate+·O$_2^-$ by the reduction of ferricytochrome C.

The experiments are divided into three groups. In the first group, 50 μmoles of xanthine, 0.0217 units/mg XO, 0.1 mM EDTA are mixed in a total volume of 1.0 ml Hank's Balanced Salt Solution (HBSS). This generated 64 ±8 nmoles oxygen. In the second group, 0.3125 units/mg SOD and 1,300 units catalase are added to the reagents employed in group 1; this yields 19.4 nmoles oxygen. Significant inhibition of free radical formation by the SOD and catalase is thus observed. In the third group, chlorine dioxide is substituted for the SOD and catalase in the same system; a chlorine dioxide concentration of about 7.5 ppm inhibits free radical formation by 74% and at a concentration of 15 ppm, by 100%.

It can be seen from the data that solutions of the invention clearly scavenge free radicals.

EXAMPLE 4

A lactic acid-activated chlorite solution is prepared by mixing 0.25% sodium chlorite with 1.5% lactic acid, which yields 150 to 600 ppm ClO$_2$. The solution inhibits fibroblast proliferation in rat fetal lung fibroblasts.

If the solution is prepared in the presence of a phosphate buffer which immediately neutralizes the lactic acid, the formation of chlorine dioxide is inhibited in the system. The solution has no inhibitory effect with rat fetal lung fibroblasts. Thus, it is not chlorite ion that is operative, but ClO$_2$.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

I claim:

1. A method for the treatment or prevention of microbial infections in a mammal having a peritoneal cavity catheter comprising infusing into the cavity or around the catheter an effective amount of a composition that is compatible with the peritoneal cavity comprising a pharmacologically acceptable carrier that is a peritoneal dialysis solution and chlorine dioxide in an amount ranging from greater than 125 ppm to about 1000 ppm, where the molar ratio of chlorine dioxide to any residual chlorite in the composition is at least 5:1 and the pH of the composition is about 5 to 7.5.

2. A method according to claim 1 wherein the chlorine dioxide is produced by reacting an acid with an alkali metal chlorite.

3. A method according to claim 2 wherein the chlorine is sodium chlorite.

4. A method according to claim 2 wherein the acid is an organic acid selected from the group consisting of citric acid, malic acid, lactic acid, mandelic acid, tartaric acid, and mixtures thereof.

5. A method according to claim 3 wherein the acid is lactic acid.

6. A method for irrigating a peritoneal cavity wound to disinfect the wound and promote healing, comprising infusing the wound with a composition that is compatible with the peritoneal cavity comprising greater than 125 ppm to 1000 ppm chlorine dioxide in a pharmaceutically acceptable carrier having a pH of about 5 to about 7.5, provided that the molar ratio of chlorine dioxide to chlorite in the composition is at least 5:1.

7. A method according to claim 6 wherein the wound is a surgical wound.

8. A method according to claim 7 wherein the composition contains from greater than 125 to about 250 ppm chlorine dioxide.

9. A method according to claim 7 wherein the composition contains from greater than 125 to about 600 ppm chlorine dioxide.

10. A method according to claim 7 wherein the wound contains an indwelling catheter.

11. A method according to claim 6 wherein the composition contains chlorine dioxide generated by reacting up to about 0.25% of a water-soluble chlorite selected from the group consisting of alkali metal chlorites, alkaline earth metal chlorites, and mixtures thereof, with a sufficient amount of acid to yield a chlorine dioxide concentration of from greater than 125 to 600 ppm.

12. A method according to claim 11 wherein the chlorite is sodium chlorite.

13. A method according to claims 11 wherein the chlorine dioxide concentration is from about 150 to 600 ppm.

14. A method according to claim 6, wherein the chlorine dioxide is generated by reaction of an acid with a water-soluble chlorite selected from the group consisting of alkali metal chlorites, alkaline earth metal chlorites, and mixtures thereof.

15. A method according to claim 14 wherein the acid is a mineral acid selected from the group consisting of sulfuric acid, hydrochloric acid, and phosphoric acid.

16. A method according to claim 14 wherein the acid is an organic acid selected from the group consisting of citric acid, malic acid, lactic acid, mandelic acid, tartaric acid, and mixtures thereof.

17. A method according to claim 14 wherein the composition further comprises isotonic chloride ion.

18. A method according to claim 14 wherein the reaction is carried out in the presence of a heat-activated saccharide compound prepared by heating a saccharide selected from the group consisting of glucose, galactose, mannose, ribose, rhamnose, lactose, sucrose, maltose, and mixtures thereof, to a temperature of from about 50° C. to about 150° C. for at least about 1 minute.

19. A method for treating or preventing a microbial infection in the peritoneal cavity of a mammal comprising infusing into the cavity an effective amount of a composition comprising chlorine dioxide in a pharmacologically acceptable carrier, wherein the molar ratio of chlorine dioxide to chlorite in the composition is at least 5.1, wherein the composition contains from greater than 125 ppm to about 1000 ppm chlorine dioxide and is compatible with the peritoneal cavity.

20. A method according to claim 19 wherein the chlorine dioxide in the composition is produced by the reaction of a chlorine dioxide generating compound and an acid.

21. A method according to claim 20 wherein the chlorine dioxide generating compound is a water-soluble chlorite selected from the group consisting of an alkali metal chlorite, an alkaline earth metal chlorite, and mixtures thereof.

22. A method according to claim 21 wherein the chlorine dioxide in the composition is produced by a process selected from the group consisting of:
   (a) reaction of a chlorite with a mineral acid and adjustment of the pH to about 5 to about 7.5;
   (b) reaction of a chlorite with an organic acid having a pK of from about 2.8 to about 4.2; and
   (c) reaction of a chlorite with a saccharide, which has been heat-activated by heating the saccharide to a temperature of from about 50° C. to about 150° C. for at least about 1 minute, in a solution in the presence of an organic acid having a pK of from about 2.8 to about 4.2 and a pH below about 5.5.

23. A method according to claim 22 wherein the organic acid is lactic acid.

24. A method according to claim 22 wherein the saccharide is selected from the group consisting of glucose, galactose, mannose, ribose, rhamnose, lactose, sucrose, maltose, and mixtures thereof.

25. A method according to claim 22 wherein the chlorite is sodium chlorite.

* * * * *